(12) United States Patent
Khalili

(10) Patent No.: US 6,228,121 B1
(45) Date of Patent: May 8, 2001

(54) PROSTHESIS SYSTEM AND METHOD OF IMPLANTING

(75) Inventor: Farid Bruce Khalili, Chestnut Hill, MA (US)

(73) Assignee: Depuy Othopedics, Inc., Warsaw, IN (US)

( * ) Notice: Subject to any disclaimer, the term of this patent is extended or adjusted under 35 U.S.C. 154(b) by 0 days.

(21) Appl. No.: 09/337,101

(22) Filed: Jun. 21, 1999

(51) Int. Cl.[7] ........................................ A61F 2/32
(52) U.S. Cl. ........................... 623/22.36; 623/22.35; 623/22.24
(58) Field of Search ................ 623/22.11, 22.15, 623/22.21, 22.35, 22.36, 22.37, 22.39, 22.4, 22.43, 16.11, 18.11, 22.17, 22.24, 22.34

(56) References Cited

U.S. PATENT DOCUMENTS

| | | |
|---|---|---|
| 4,840,632 | 6/1989 | Kampner . |
| 4,881,532 | 11/1989 | Borig et al. . |
| 4,888,022 | 12/1989 | Huebsch . |
| 4,892,550 | 1/1990 | Huebsch . |
| 5,002,578 | 3/1991 | Luman . |
| 5,021,062 | 6/1991 | Adrey et al. . |
| 5,211,666 | 5/1993 | Fetto . |
| 5,259,249 | 11/1993 | Fetto ..................................... 73/794 |
| 5,417,696 | 5/1995 | Kashuba et al. ........................ 606/9.1 |
| 5,534,032 | 7/1996 | Hodorek . |
| 5,540,697 | 7/1996 | Rehmann et al. ....................... 606/91 |
| 5,571,193 | 11/1996 | Kampner . |
| 5,580,352 | 12/1996 | Sekel . |
| 5,584,837 | 12/1996 | Petersen ................................. 606/91 |
| 5,725,588 | * 3/1998 | Errico et al. ....................... 623/22.36 |
| 5,733,338 | 3/1998 | Kampner . |
| 5,791,899 | 8/1998 | Sachdeva et al. .................... 433/173 |

FOREIGN PATENT DOCUMENTS

| | | | |
|---|---|---|---|
| 0341199 | * 11/1989 | (EP) | ....................... 623/22 |
| 2685192 | * 6/1993 | (FR) | ....................... 623/22 |

* cited by examiner

*Primary Examiner*—Jeffrey A. Smith
(74) *Attorney, Agent, or Firm*—Nutter, McClennen & Fish, LLP

(57) ABSTRACT

A prosthetic joint system includes a body having at least one aperture into which an elongate sleeve component is engageable. A screw for securing the body to bone is insertable into the bone via a bore in the sleeve. The bore has a length that is sufficient to accommodate movement of the screw as the prosthesis subsides over time. More particularly, the sleeve allows the screw head to move longitudinally such that the screw is prevented from damaging an inner member of the prosthesis system that provides an articulation surface for a corresponding prosthetic joint component. In one embodiment, a prosthesis system includes an acetabular cup for a prosthetic hip joint.

17 Claims, 5 Drawing Sheets

PROSTHESIS SYSTEM AND METHOD OF IMPLANTING

CROSS REFERENCE TO RELATED APPLICATION

Not Applicable.

STATEMENT REGARDING FEDERALLY SPONSORED RESEARCH

Not Applicable.

FIELD OF THE INVENTION

The present invention relates generally to prosthetic components, and more particularly, to prosthetic joints.

BACKGROUND OF THE INVENTION

Joint arthroplasty is a well known surgical procedure by which a diseased and/or damaged natural joint is replaced by a prosthetic joint. Joint arthroplasty is commonly performed for hips, knees, elbows, and other joints. The health and condition of the joint to be replaced dictate the type of prosthesis necessary to replace the natural joint. For example, in a total hip arthroplasty an acetabular cup may be implanted in the pelvis to replace the natural acetabulum.

To implant an acetabular cup, an acetabular cavity is reamed in the acetabulum. The reamed cavity generally conforms to an outer surface of the acetabular cup. The acetabular cup is then inserted into the formed cavity and is then further secured by mechanical means, such as one or more fixation screws. The acetabular cup is positioned in the pelvis at a relatively fixed orientation with respect to patient anatomy and should remain stable.

FIGS. 1–4 show one type of prior art acetabular cup 10 implanted in a patient's acetabulum 12. The cup 10 includes a hemispherical outer member 14 for interfacing to bone and a mating inner member 16 for providing an articulation surface for the ball 18 of a femoral component 20. The inner member 16 is formed from polyethylene, for example, to provide a durable, low friction interface for allowing the femoral component to move freely. Apertures 22 are formed in the outer member 14 of the cup to provide passageways for fixation screws 24 that secure the acetabular cup 10 to the bone.

While the apertures allow the fixation screws to penetrate bone, the screws must be inserted at locations corresponding to the apertures. In addition, the fixations screws must be introduced into the bone within a limited angular range to allow proper seating of the screw head in the aperture.

Further, while the implanted cup may initially be secured in position, movement of the implanted acetabular cup over time can contribute to erosion of the surrounding bone. One effect of such bone erosion is the loosening of the acetabular cup, allowing it to shift in position. More particularly, the implanted cup tends to subside into the surrounding bone so as to adversely affect conditions in the prosthetic joint. Typically, an implanted acetabular cup will subside several millimeters within a few years after implantation, which can result in one or more fixation screw impinging on the cup liner. Screw/liner contact can cause fretting of the liner and possibly catastrophic failure of the liner.

For example, as shown in the prior art prosthetic hip joint of FIG. 4, as the cup 10 subsides into the surrounding bone a head 26 of the fixation screw 24 begins to impinge upon the polyethylene inner cup member 16. The action of the screw 24 against the polyethylene inner member 16 as the joint is subjected to loads may cause wear debris to develop, which can ultimately result in osteolysis within the joint. In extreme cases, the screw 24 can fracture the inner member 16 causing catastrophic failure of the joint.

It would, therefore, be desirable to provide an implantable prosthesis system having features to optimize the positioning of fixation screws into bone, to minimize the effects of implant subsidence into the surrounding bone, and to increase safety margins.

SUMMARY OF THE INVENTION

The present invention provides a prosthetic joint system that enhances the long term fixation properties of the implant by providing a structure to allow fixation screws to be inserted at a range of angles and to accommodate subsidence of the prosthesis into bone. Although, the invention is primarily shown and described as an acetabular cup implantation system, it is understood that the invention has other applications as well, such as for use with prosthetic knee systems.

In one embodiment, an implantable prosthesis system includes an acetabular cup having a convex outer component for interfacing with bone and an inner component that is matable with the outer component to provide an articulation surface for a corresponding femoral component. The acetabular cup includes at least one aperture to provide a passageway for a fixation element, such as a screw, to secure the cup to bone. A plurality of sleeve components are provided to mate with the apertures formed in the outer component. Each sleeve is of a substantially elongate shape having an outer surface and a longitudinal bore extending therethrough from a proximal opening to a distal opening in the sleeve. The longitudinal bore is adapted to receive a fixation element, e.g., a bone screw, such that a head of the screw seats within the sleeve adjacent the distal opening of the sleeve. Each sleeve is adapted to mate with one of the apertures such that the distal opening of the sleeve is spaced away from an outer surface of the acetabular cup.

The sleeve component can be positioned at a range of angles with respect a central axis of an aperture of the acetabular cup with which it is mated, thus allowing the fixation screws to be inserted into a desired region of bone. In addition, the sleeve compensates for subsidence of the implanted acetabular cup by providing a region to accommodate longitudinal movement of the fixation screw to prevent the screw head from contacting, and thereby possible damaging, the inner cup component.

To implant the acetabular cup system, an acetabular cavity is formed in the patient's acetabulum and the prosthetic cup component is inserted into the formed cavity. The surgeon then drills one or more holes in the bone via the apertures in the cup outer surface at predetermined angles to optimize fixation of the cup to bone by way of the screws. The formed holes are then used to align a larger diameter drill for enlarging a portion of the holes to receive the sleeve components. The sleeve components are engaged with respective fixation screws, which are then rotated into the holes formed in the bone to secure the acetabular cup to the acetabulum.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
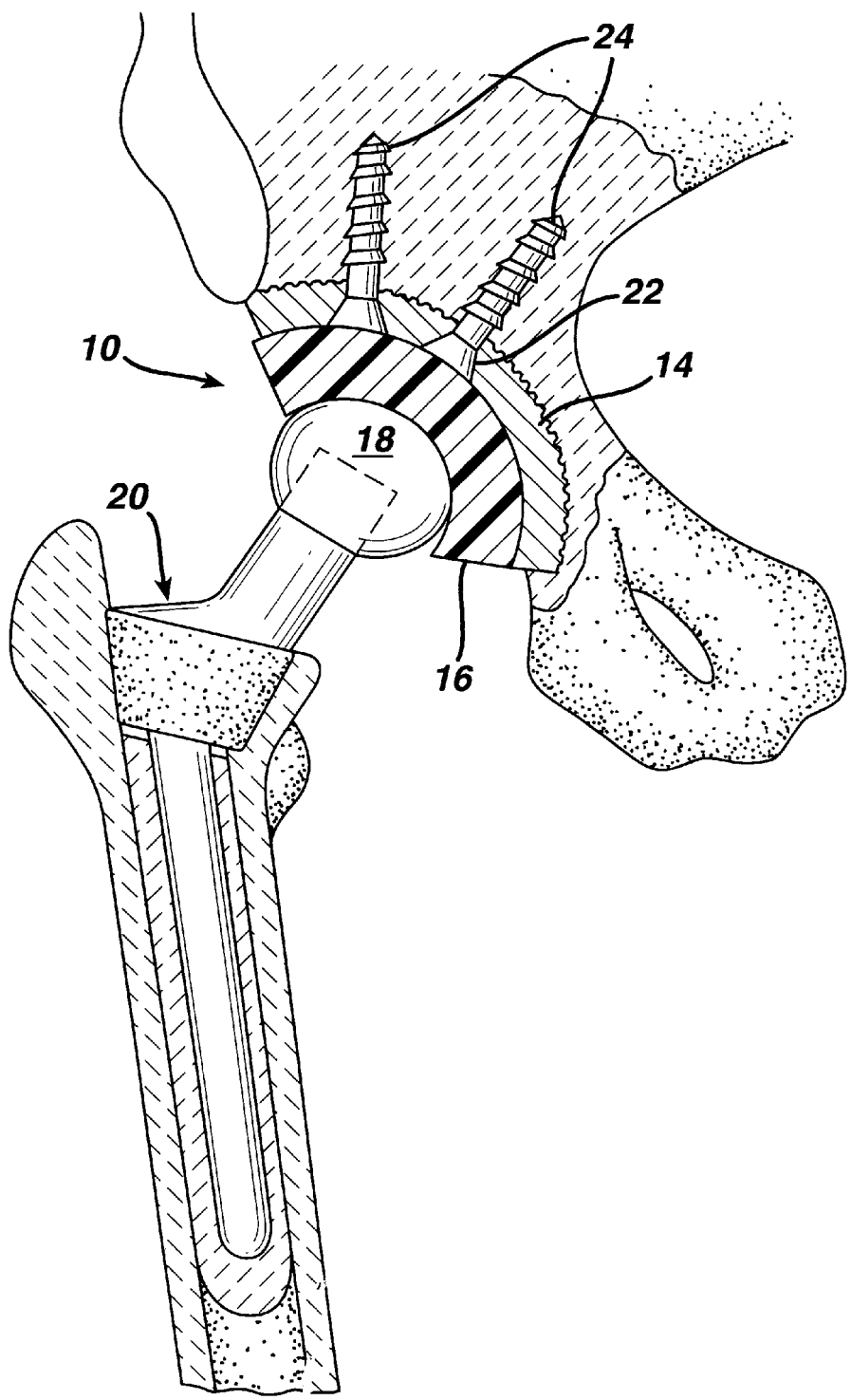
FIG. 1 is a partly cross-sectional view of a prior art prosthetic hip joint.
Figure 2:
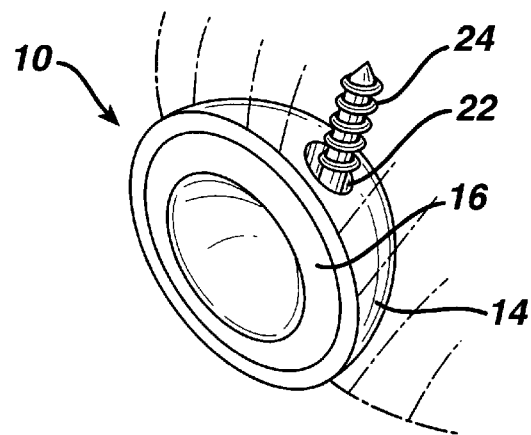
FIG. 2 is a diagrammatic view of a prior art acetabular cup that forms a part of the prior art prosthetic hip joint of FIG. 1.
Figure 3:
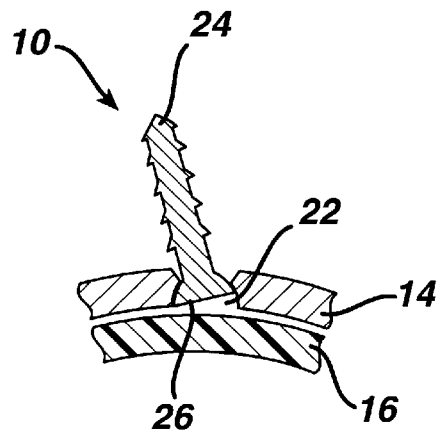
FIG. 3 is a cross-sectional view of a part of the prior art acetabular cup of FIG. 2 further showing a screw in a first position.
Figure 4:
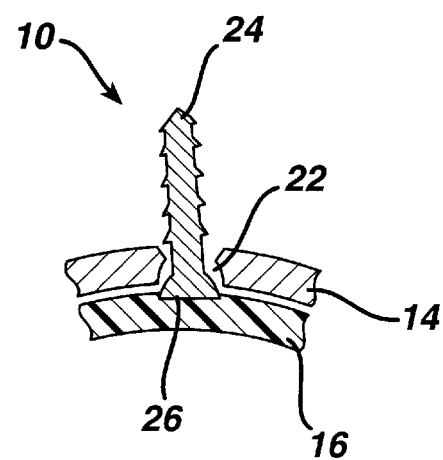
FIG. 4 is a cross-sectional view of a part of the prior art acetabular cup of FIG. 2 further showing a screw in a second position.
Figure 5:
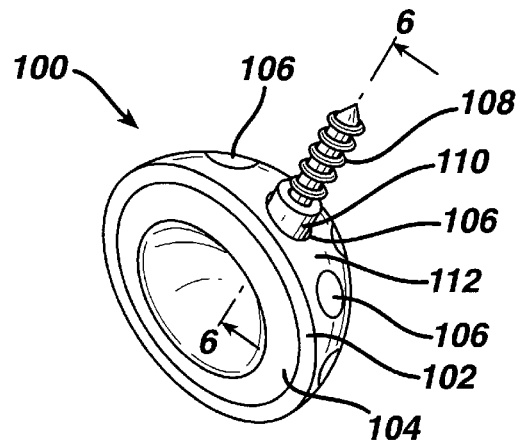
FIG. 5 is a perspective view of an acetabular cup system in accordance with the present invention.

FIG. 5 shows an acetabular cup system 100 in accordance with the present invention. The system includes a convex outer member 102 and an inner bearing member 104. A series of apertures 106 are formed in and extend through the outer member 102 to provide a passageway for fixation screws 108 into the surrounding bone. One or more sleeve components 110 are provided, each of which is matable within a respective aperture. The sleeve member 110, when mated with an aperture of the outer member 102, is effective to accommodate subsidence of the implant into bone over time by preventing damage to the inner member 104 as a result of impingement of the screw 108 against the inner member due to migration of the implanted cup. In addition, the sleeve component 110 can be positioned at various angles in relation to the implanted acetabular cup to optimize placement of screws within bone.

The outer member 102 of the acetabular cup is generally hemispherical so as to facilitate its implantation into a complementary cavity reamed in a patient's acetabulum. In general, an outer surface 112 of the cup interfaces with bone to secure the cup within the formed acetabular cavity. The contour of the outer member 102 and/or formed acetabular cavity can be adapted for an interference fit of the cup if desired. It is understood that the outer surface 112 of the cup can include various surface features to enhance bone ingrowth.

The apertures 106 are formed at various locations in the outer member 102 of the cup to provide a surgeon with a range of options for inserting the fixation screws 108 through the acetabular cup into the surrounding bone. The screws 108 enhance fixation of the implanted cup 100 to improve the likelihood of achieving long term fixation of the prosthetic component.

Figure 6:
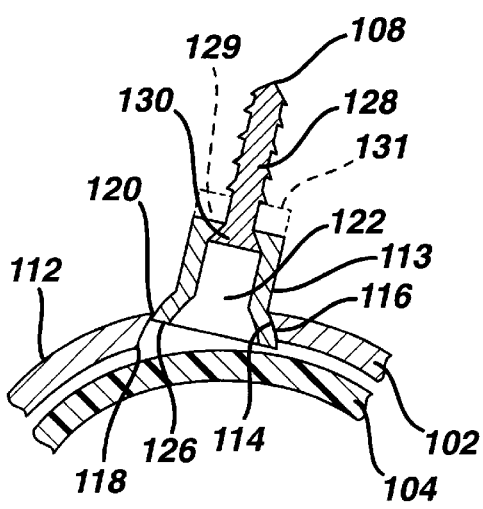
FIG. 6 is a cross-sectional view of a part of the acetabular cup system of FIG. 5 along line 6—6 with a screw, which forms a part of the system, shown in a first position.
Figure 7:
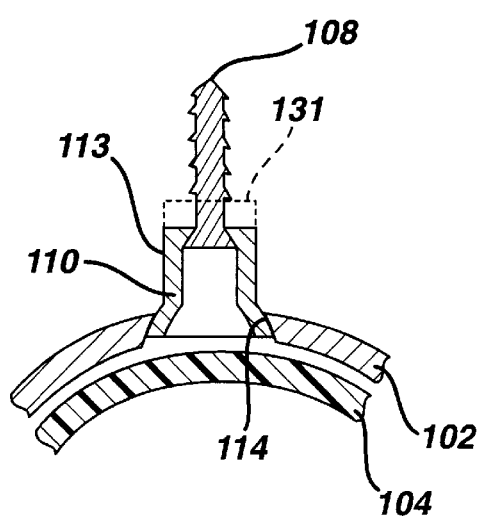
FIG. 7 is a cross-sectional view of a part of the acetabular cup system of FIG. 5 along line 6—6 with a screw, which forms a part of the system, shown in a second position.
Figure 9:
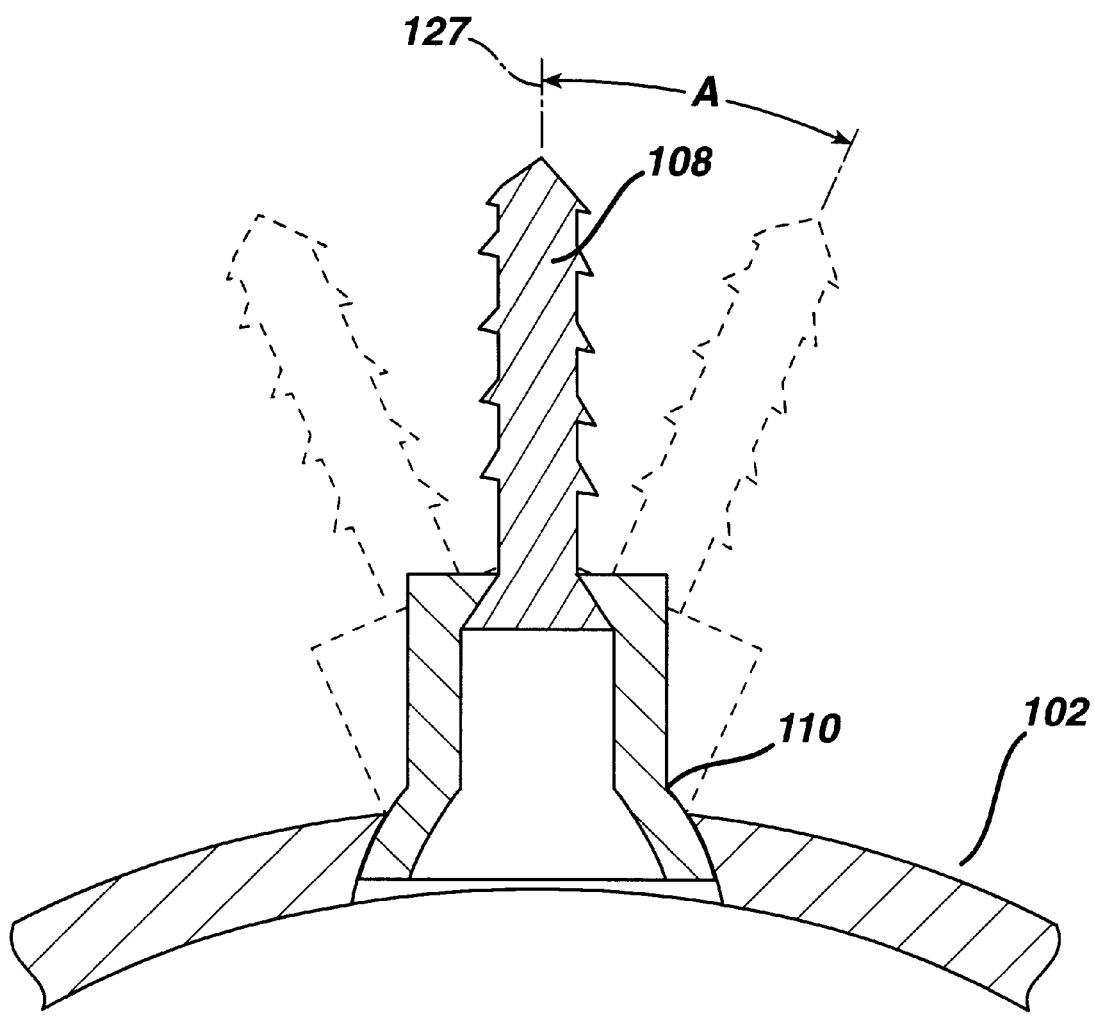
FIG. 9 is a cross-sectional view of the sleeve component of FIG. 8 shown mated with an acetabular cup and oriented at a range of angles.

As shown in FIGS. 6, 7, and 9, the aperture wall 114 engages the sleeve component 110 and prevents its passage through the cup outer member 102. In general, the respective geometries of the sleeve component 110 and the aperture wall 114 should, upon engagement, cooperate to position a distal end 113 of the sleeve 110 a predetermined distance from the outer surface 112 of the acetabular cup. A proximal or mating end 126 of the sleeve includes a structure adapted for seating in the aperture wall 114. The sleeve/aperture structure should also allow the sleeve to be positioned at a selected angle with respect to the cup outer surface 112. Exemplary structures for the sleeve mating end 126 include arcuate, spherical, and tapered.

In an exemplary embodiment, the aperture wall 114 is tapered so as mate with a complementary mating surface 116 at a proximal or mating end 126 of the sleeve component. The taper is such that the inner-most end 118 of the aperture is larger than the outer-most end 120. It is understood that the taper angle can vary about the longitudinal axis of the sleeve to facilitate seating of the mating end 126 within the aperture wall at a predetermined position.

The structure of the aperture wall 114 and the complementary sleeve mating surface 116 allows the sleeve 110 to be positioned at a range of angles in relation to the outer member 102 of the acetabular cup, as shown in FIG. 9. By providing a range of angles, the sleeve component 110 can be positioned so as to provide access to desired regions of bone in the acetabular cavity, such as those having the deepest and/or best quality bone. In an exemplary embodiment, an angle A formed by a longitudinal axis 127 of the sleeve and a normal to the convex outer component 102, i.e., a central axis of the aperture, ranges from zero degrees (axis 127 coincident with the normal) to about ten degrees. It is understood that the sleeve 110 can be rotated in any direction from the normal for allowing the surgeon to insert the screw into a bone at a selected angle for optimal fixation of the cup.

Figure 8:
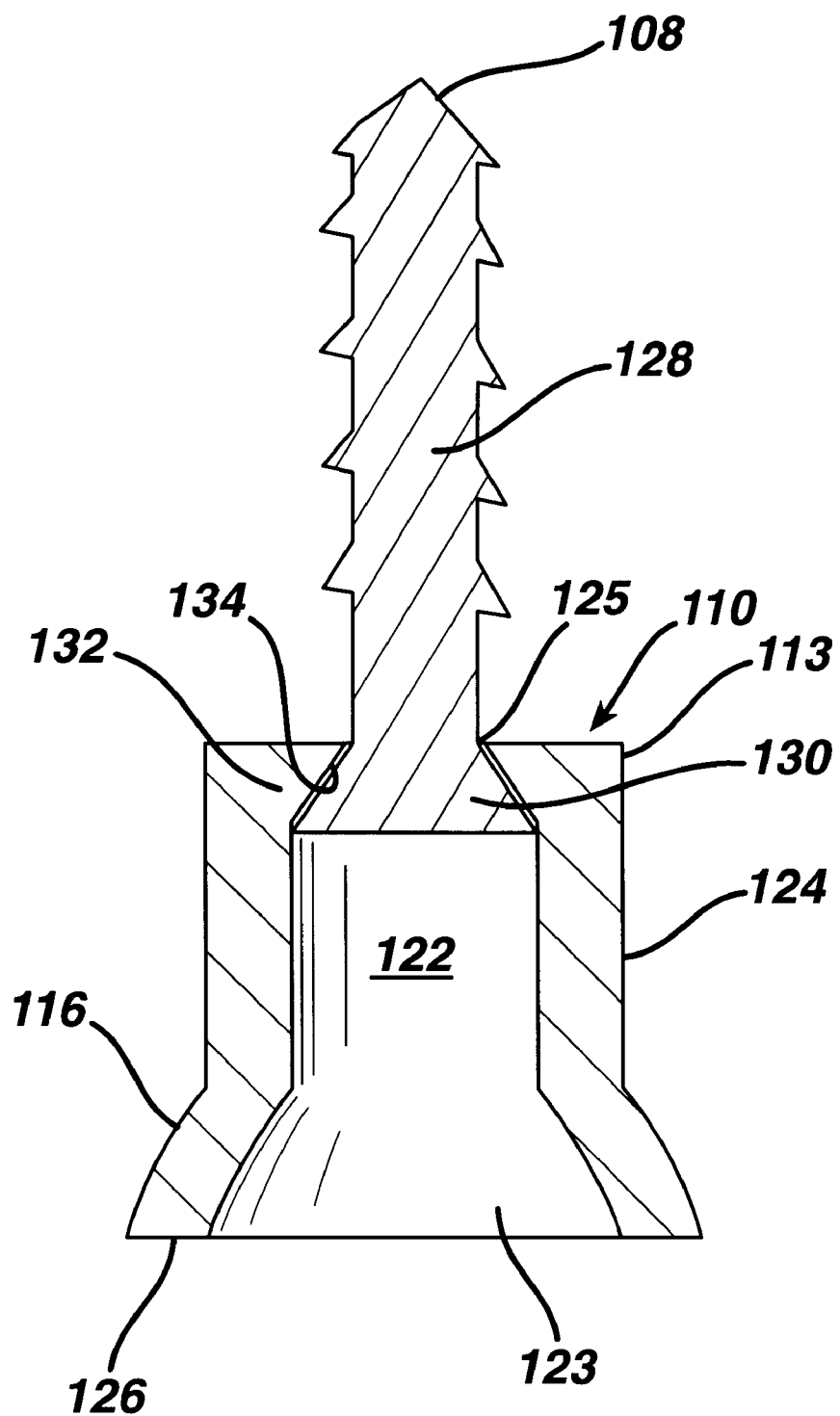
FIG. 8 is a cross-sectional view of a sleeve component that forms a part of the acetabular cup system of FIG. 5.

Referring again to FIG. 8, the elongate sleeve 110 has a longitudinal bore 122 formed therein through which the screw 108 passes. The bore extends from a proximal opening 123 to a distal opening 125. In an intermediate region 124 of the sleeve, the bore 122 has a diameter that allows passage of a threaded region 128 and head 130 of the fixation screw 108. In an exemplary embodiment, the bore 122 is flared, thus increasing in diameter, at the proximal opening 123 so as to facilitate insertion of the screw into the sleeve. The distal opening 125 of the bore has a tapered seating surface 132 that complements the geometry 134 of the screw head 130 such that the screw is properly seated within the sleeve 110 and is prevented from exiting the sleeve 110.

To implant the acetabular cup system 110, a cavity is reamed in the patient's acetabulum using conventional techniques and instruments. In one embodiment, the formed acetabular cavity is adapted for interference fit engagement with the acetabular cup 10. After the cup is inserted into the formed cavity, the surgeon drills holes in the bone via the apertures 106 in the cup outer member. The holes are formed at an angle to allow insertion of the fixation screws into selected regions of bone, such as those having the deepest and/or best quality bone. The holes are sized to be slightly smaller than the screws to facilitate insertion of the screws into the bone. A larger diameter drill is then used to enlarge an upper region of the formed holes so as to form enlarged and unenlarged regions of each hole. The enlarged region 129 of the hole is shown in phantom in FIG. 6. The enlarged region of the hole conforms to an outer diameter of the sleeve intermediate portion 124, which protrudes from the cup outer surface. After implantation, there is a gap between an end 131 of the enlarged region and the distal end 113 of the sleeve.

The sleeve components 110 are then engaged with respective fixation screws 108. The surgeon then inserts the sleeve/screw assembly into an aperture 106 in the cup and rotates the screw within the formed hole until the mating surface 116 of the sleeve is securely seated within the aperture 106. The intermediate portions 124 of the sleeve are disposed within the enlarged regions of the holes. Each sleeve/screw assembly is secured in place to completely affix the outer member 102 of the acetabular cup to the bone.

The polyethylene inner member 104 is then mated to the cup outer member 102 using conventional techniques and components, such as a bearing insert. The implanted acetabular cup can then receive a corresponding femoral component.

As the acetabular cup subsides into bone (FIG. 7), the gap between the distal end 113 of the sleeve and the end 131 of the enlarged region of the hole decreases. As the gap shrinks, the fixation screw 108 recedes from the bone and the head 130 of the screw moves longitudinally in the sleeve bore. However, the length of the bore is of sufficient length to accommodate movement of the screw without the screw head 130 contacting the bearing member 104.

It is understood that the overall dimensions of the acetabular cup system components can vary. In an exemplary embodiment, the sleeve component 110 has a length in the range of about eleven millimeters to about sixteen millimeters and protrudes about five millimeters to about ten millimeters from the outer surface 112 of the implanted cup. Initially, the screw is inserted into bone to provide a distance from the head 130 of the screw 108 to the surface of the inner member 104 that can range from about seven millimeters to about twelve millimeters.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implantable prosthesis system, comprising:
   a body having an inner surface and an outer, mounting surface with at least one aperture extending therebetween;
   an inner member having a first surface matable against the inner surface of the body and a second, opposed bearing surface;
   at least one sleeve having a substantially elongate shape and being matable with the at least one aperture of the body, the at least one sleeve having an outer surface with a proximal end, a distal end, and a cylindrically shaped intermediate region between the proximal end and distal end, the at least one sleeve further including a longitudinally oriented bore extending therethrough from a proximal opening to a distal opening, and being matable with the at least one aperture such that the distal opening of the at least one sleeve is spaced from the outer, mounting surface of the body; and
   at least one elongate fixation element mountable within the at least one sleeve to secure the body to bone, the at least one fixation element having a proximal head portion seatable within the at least one sleeve adjacent the distal opening of the at least one sleeve and a shaft portion extending distally from the head portion.

2. The system according to claim 1, wherein the sleeve is matable within the at least one aperture of the body at a selectable angle relative to a central axis of the at least one aperture.

3. The system according to claim 1, wherein the body is an acetabular cup.

4. The system according to claim 1, wherein an outer wall of the at least one sleeve defines a proximal end having a flared mating surface.

5. The system according to claim 4, wherein the at least one aperture is defined by an aperture wall having a tapered surface effective to seat the flared mating surface of the at least one sleeve.

6. The system according to claim 1, wherein a distal end of the bore of the at least one sleeve is tapered to form a fixation element seating surface.

7. The system according to claim 1, wherein the distal opening of the at least one sleeve is spaced from the outer surface of the body by a distance in the range from about five millimeters to about fifteen millimeters.

8. The system according to claim 1, wherein the at least one fixation element is a bone screw.

9. An acetabular cup system, comprising:
   a first member having a convex outer surface and a concave inner surface with at least one aperture extending between the inner and outer surfaces of the first member;
   a convex bearing member having an outer surface matable against the inner surface of the first member and an inner, bearing surface; and
   at least one sleeve component having a substantially elongate shape and being matable within the at least one aperture of the first member, the at least one sleeve component having an outer surface with a flared proximal end adapted to seat within the at least one aperture of the first member, a distal end, a cylindrically shaped intermediate region between the proximal end and distal end, and a longitudinal bore extending through the at least one sleeve component from the proximal end to the distal end thereof, the longitudinal bore defining a screw head-seating surface at the distal end of the bore.

10. The system according to claim 9, further comprising at least one bone screw member having a proximal head adapted to seat on the screw head-seating surface of the at least one sleeve component.

11. The system according to claim 9, wherein the at least one sleeve component is matable within the at least one aperture of the first member at a selectable angle relative to a central axis of the at least one aperture, wherein the angle ranges from about zero degrees to about twenty degrees.

12. The system according to claim 9, wherein the screw head seating surface of the at least one sleeve component is formed by a distally tapered portion of the longitudinal bore.

13. The system according to claim 9, wherein the at least one sleeve component has a length that ranges from about eleven millimeters to about twenty millimeters.

14. The system according to claim 9, wherein the distal opening of the at least one sleeve component protrudes from the outer surface of the first member a distance of between about seven millimeters and about sixteen millimeters.

15. A method of implanting a prosthesis system, comprising:
   reaming a cavity in bone;
   implanting a prosthetic component in the cavity, the prosthetic component having an aperture;
   forming a hole in the bone via the aperture, the hole having a first diameter;
   enlarging the diameter of a selected portion of the hole so as to form an enlarged portion and an unenlarged portion;
   inserting a sleeve component into the enlarged portion of the hole;

inserting a fixation screw into the unenlarged portion of the hole; and rotating the fixation screw to affix the prosthetic component to the bone.

16. The method according to claim 15, wherein the hole can be formed in the bone at a selected angle.

17. The method according to claim 16, wherein the angle of the hole with respect to the prosthetic component can range from ninety degrees to about plus or minus seventy degrees.

* * * * *